(12) United States Patent
Kikuchi et al.

(10) Patent No.: US 6,486,449 B2
(45) Date of Patent: Nov. 26, 2002

(54) HEATER PATTERNS FOR PLANAR GAS SENSORS

(75) Inventors: Paul C. Kikuchi, Fenton, MI (US); Lone-Wen F. Tai, Rochester Hills, MI (US); Walter T. Symons, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/020,545

(22) Filed: Oct. 29, 2001

(65) Prior Publication Data

US 2002/0079308 A1 Jun. 27, 2002

Related U.S. Application Data

(63) Continuation of application No. 09/740,776, filed on Dec. 19, 2000, now Pat. No. 3,365,880.

(51) Int. Cl.[7] .................................................. H05B 3/02
(52) U.S. Cl. ....................................................... 219/479
(58) Field of Search ................................ 219/479, 543, 219/209, 505, 539, 549, 579; 338/22 R, 22 SD, 23, 24; 73/204.26, 204.23, 204.25

(56) References Cited

U.S. PATENT DOCUMENTS

| | | | |
|---|---|---|---|
| 4,146,957 A | | 4/1979 | Toenshoff |
| 5,038,609 A | | 8/1991 | Kumada |
| 5,051,718 A | * | 9/1991 | Satake et al. .............. 338/22 R |
| 5,057,811 A | * | 10/1991 | Strott et al. ............... 338/22 R |
| 5,064,693 A | * | 11/1991 | Hayakawa et al. .......... 204/421 |
| 5,172,466 A | * | 12/1992 | Friese et al. ................... 29/612 |
| 5,288,389 A | | 2/1994 | Yamada et al. |
| 5,406,246 A | * | 4/1995 | Friese et al. ................... 29/612 |
| 5,561,411 A | * | 10/1996 | Kuzuoka ................. 338/22 SD |
| 5,823,680 A | * | 10/1998 | Kato et al. ..................... 338/17 |
| 5,895,591 A | | 4/1999 | Kojima et al. |
| 5,965,049 A | * | 10/1999 | Carlet ......................... 219/505 |
| 6,194,693 B1 | * | 2/2001 | Shirai et al. ................. 219/543 |

* cited by examiner

Primary Examiner—Henry Bennett
Assistant Examiner—Vinod D. Patel
(74) Attorney, Agent, or Firm—Vincent A. Cichosz

(57) ABSTRACT

A heater for a gas sensor has a first thermistor element and a second thermistor element arranged in an electrically parallel configuration. Each thermistor element may be deposited onto a substrate such that the first thermistor element extends about a perimeter of the substrate and the second thermistor element extends across a portion of the substrate intermediate the perimeter of the substrate. The thermistor elements are preferably fabricated of materials having differing thermal coefficients of resistivity. A method of heating the gas sensor includes disposing the two thermistor elements in an electrically parallel configuration over a surface of the substrate and passing an electric current through the elements.

7 Claims, 2 Drawing Sheets

HEATER PATTERNS FOR PLANAR GAS SENSORS

CROSS REFERENCE TO RELATED APPLICATION

This application is a continuation of U.S. patent application Ser. No. 09/740,776 filed on Dec. 19, 2000 now U.S. Pat. No. 6,365,880, which is incorporated herein by reference.

TECHNICAL FIELD

This disclosure relates to planar gas sensors, and, more particularly, to heater patterns for planar gas sensors that yield a reduction in the incidence of cracking attributable to tensile stresses at the edges of the planar gas sensors.

BACKGROUND

Gas sensors, and in particular oxygen sensors, are used in combustion engines to control the air/fuel ratio in the combustion chamber so that the air/fuel ratio remains at or near its proper stoichiometric value. Maintaining the proper stoichiometric value allows for the improvement of fuel consumption and the minimization of impurities in an exhaust gas. An oxygen sensor typically includes an oxygen sensing element having an ion-conductive solid electrolytic plate on which porous electrodes are disposed. A difference in potential corresponding to the difference in oxygen content between the gas and the reference air is generated by the oxygen sensing element, is quantified, and is used to adjust the air/fuel ratio in the combustion chamber.

The proper functioning of the oxygen sensing element is typically dependent upon its temperature. Because a significant amount of time is often required for the oxygen sensor to become active after startup of the engine, the air/fuel ratio is difficult to control during that time. Heaters are, therefore, oftentimes incorporated into the oxygen sensing system to more quickly bring the oxygen sensing elements up to a temperature at which the most efficiency can be realized.

Typical heaters in planar sensors are formed in various patterns on one face of the oxygen sensing element. Irregularities in the patterning of the heater trace can give rise to "hotspots". These hotspots are the primary locations for failure of the heater because of opening of the heater trace. Such a design attempts to create a uniform temperature profile across the sensor element by adjusting the heat input through patterning of a single heater trace. Heater patterns such as these are difficult to control because the balance of the heat input between the center and the edges of the pattern changes as the temperature changes. Variations in the heating profile oftentimes cause "hotspots" within the oxygen sensing element, which result in thermal shock. In such a configuration, because the oxygen sensing element is usually fabricated from a ceramic material, differing rates of expansion often cause tensile stresses to be experienced along the interfaces of the hotter and colder areas. Such tensile stresses may, over time, cause the oxygen sensing elements to fracture and function improperly, thereby communicating inaccurate information for the control of the air/fuel ratio. In such an instance, the oxygen sensor will require replacement to ensure maximum efficiency of the system operation.

BRIEF SUMMARY

A heater pattern for a heater of a gas sensor in which a temperature profile is manipulated through the use of separate thermistor elements to reduce the number of hotspots therein is described below. The heater pattern is defined by first and second thermistor elements in communication with each other in an electrically parallel configuration. In a first embodiment, the first thermistor element extends substantially about a perimeter of the substrate and is typically formed of a material having a specific thermal coefficient of resistivity. The second thermistor element extends across a portion of the substrate intermediate the perimeter of the substrate and is formed of a material having a thermal coefficient of resistivity that is higher than the thermal coefficient of resistivity of the first thermistor element. In a second embodiment, in order to further reduce the incidence of hotspots in a heater, each thermistor element is formed of first and second conductors disposed in a spaced relationship and in communication with each other through a cross conductor. The thermistor elements are screen printed onto a substrate to a thickness of about 5 microns to about 50 microns. A method of heating the gas sensor with the heater pattern includes disposing the two thermistor elements in an electrically parallel configuration over a surface of the substrate and passing an electric current through the elements.

The above-described and other features and advantages of the present invention will be appreciated and understood by those skilled in the art from the following detailed description, drawings, and appended claims.

BRIEF DESCRIPTION OF THE DRAWINGS

The apparatus and method will now be described by way of example, with reference to the accompanying drawings, which are meant to be exemplary, not limiting.

DETAILED DESCRIPTION

A heater pattern for a heater of a planar gas sensor is described herein. Although an oxygen sensor is described, the gas sensor could be a nitrogen oxide sensor, a hydrogen sensor, a hydrocarbon sensor, or a similar apparatus. Unlike heaters of the prior art, which typically include a single thermistor extending about an outer edge of the heater, the disclosed heater has a pattern disposed thereon that utilizes two conductor paths, one that extends about the outer edge of the heater and another that extends over the portion of the heater intermediate the outer edge. The patterns are arranged so as to form an electrically parallel configuration. The respective power of each leg of the parallel configuration is a function of the thermal coefficient of resistivity (TCR) of the conductive material from which each leg is fabricated. By forming each leg of the configuration such that each leg has a different TCR, the power input to each leg is variable. Variability in the power inputs allow the heat input to each leg to be self-adjusting, which allows for a more uniform temperature profile to be developed over the layer of the planar oxygen sensor on which the heater is disposed. Although the following description is drawn to a heater pattern for a planar oxygen sensor, it should be understood that the sensor into which the heater pattern could be incorporated could be a conical sensor.

Figure 1:
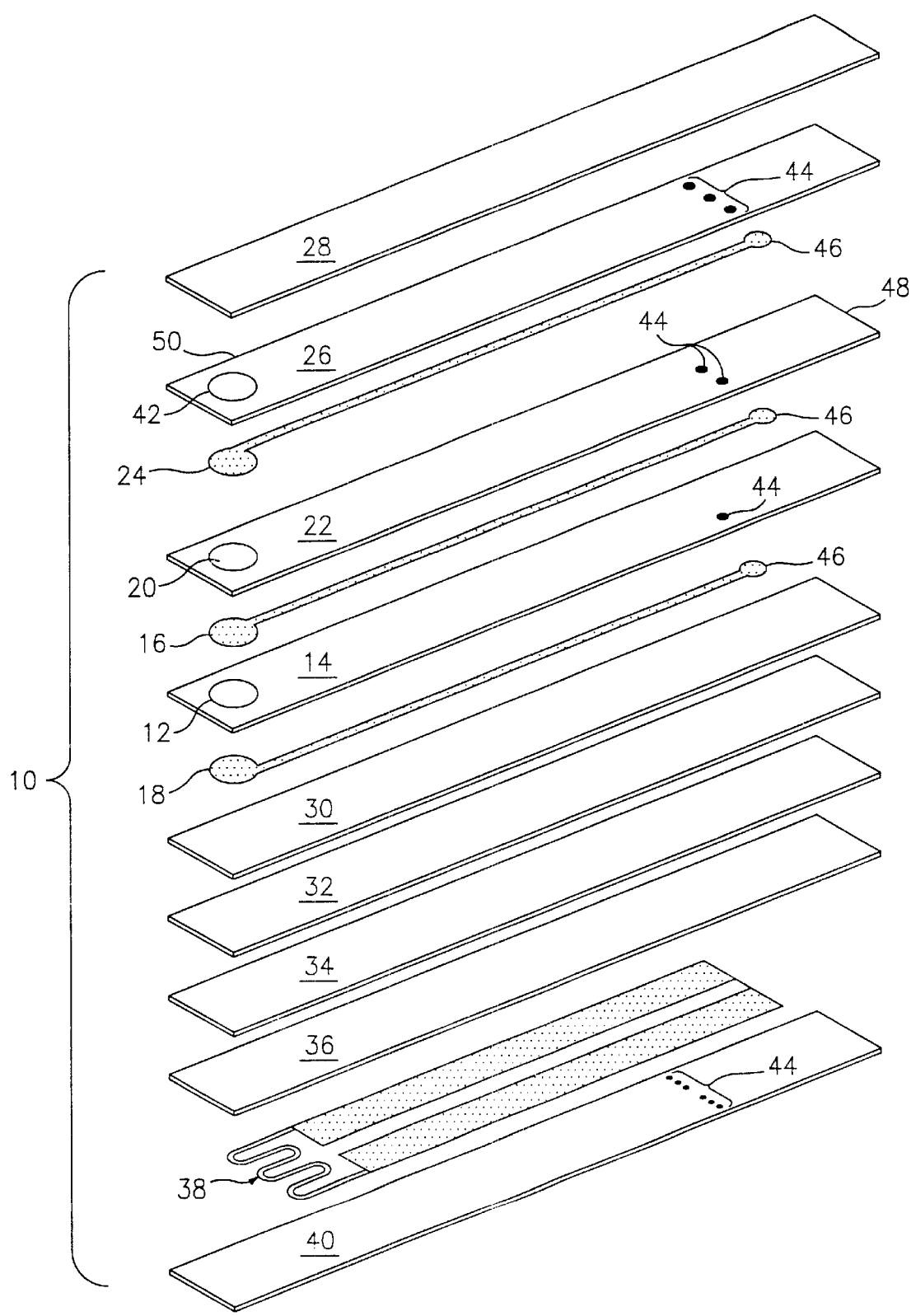
FIG. 1 is an exploded view of an embodiment of a planar oxygen sensor element.

Referring to FIG. 1, a typical arrangement of the different layers of a sensor element, shown generally at 10, is illustrated. Sensor element 10 comprises a solid electrolyte 12 disposed in a dielectric layer 14 with an inner electrode 16 and a reference electrode 18 disposed on opposite sides of solid electrolyte 12; a porous electrolyte 20 disposed in electrical communication with inner electrode 16 and disposed in a dielectric layer 22; an outer electrode 24 disposed on the side of porous electrolyte 20 opposite inner electrode 16; and a dielectric layer 26 disposed against dielectric layer 22 opposite dielectric layer 14. Sensor element 10 further comprises internal support layers 30, 32, 34, 36 disposed against dielectric layer 14; a heater, shown generally at 38, disposed between support layer 36 and a protective outer layer 40; a protective material 42 disposed in fluid communication with outer electrode 24 and within dielectric layer 26; vias 44 formed in dielectric layers 14, 22, 26, and outer layer 40; leads 46 in electrical communication with electrodes 16, 18, 24. A terminal end of sensor element 10 is shown generally at 48, and a sensor end of sensor element 10 is shown generally at 50. A heater pattern (not shown) is disposed on heater 38 and is described below with reference to FIG. 2.

Outer electrode 24, porous electrolyte 20, and inner electrode 16 form a pumping cell, while inner electrode 16, solid electrolyte 12, and reference electrode 18 form a reference cell. Oxygen in the exhaust gas enters the pumping cell through protective material 42 and diffuses through outer electrode 24 and porous electrolyte 20 to inner electrode 16, where the oxygen is ionized and pumped back out of the cell. Generally, a reference cell is used in combination with the pumping cell, but the pumping cell can be used as the only electrochemical cell in the sensor in lean-only applications. The reference cell is used to compare the partial pressure of oxygen at inner electrode 16 with a known oxygen partial pressure at reference electrode 18 in order to determine the potential that should be applied to the pumping cell. The measured current in the pumping cell will be proportional to the partial pressure of oxygen in the exhaust gas.

Leads 46 are disposed across dielectric layers 14, 22 to electrically connect the external wiring of sensor element 10 with electrodes 16, 18, 24. Leads 46 are typically formed on the same layer as the electrode to which they are in electrical communication and extend from the electrode to the terminal end 48 of the element where they are in electrical communication with the corresponding via 44. Heater 138 also includes leads (shown below with reference to FIG. 3) that are in electrical communication with vias 44.

Figure 2:
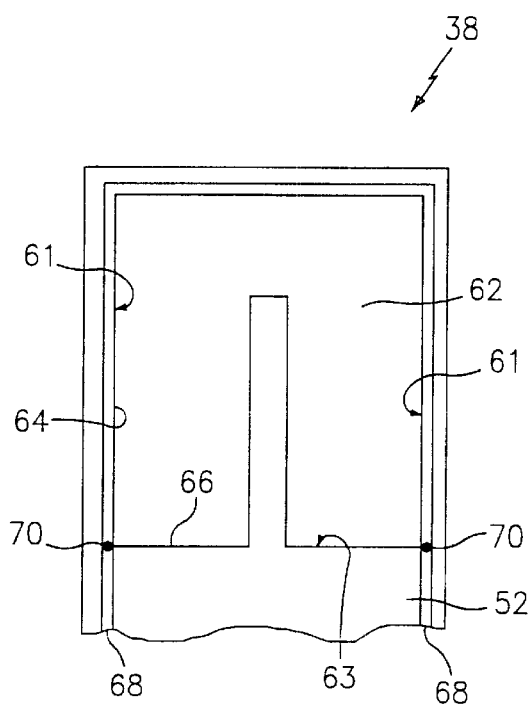
FIG. 2 is a plan view of a first embodiment of a heater pattern disposed on a substrate.

Referring now to FIG. 2, heater 38 is shown in greater detail. Heater 38 comprises a first thermistor, shown generally at 61, and a second thermistor, shown generally at 63, arranged in a heater pattern that defines a heating section 62 and leads 68. Thermistors 61, 63 are each disposed on a substrate 52 and positioned between the adjacent layers of the sensor element. Preferred materials for use as substrate 52 include, but are not limited to, alumina, alumina-based compounds, ceramics, glasses, cermets, and combinations of at least one of the foregoing materials.

Heating section 62 comprises an edge pattern 64 and a center pattern 66 arranged in the electrically parallel configuration as described above. Edge pattern 64 extends generally about an outer edge of heating section 62 that corresponds with a perimeter of substrate 52. Center pattern 66 extends from nodes 70 disposed on edge pattern 64 at opposing edges of heating section 62 substantially across a portion of heating section 62 intermediate the perimeter of substrate 52 in an electrically parallel configuration. Center pattern 66 is preferably arranged on substrate 52 substantially in the form of an inverted U shape, the ends of the legs of the U shape being in electronic communication with nodes 70. Such an arrangement maximizes the area of substrate 52 over which center pattern 66 is disposed. By maximizing the area over which center pattern 66 is disposed, the number of temperature differentials created within heating section 62 is minimized and heater 38 is provided with improved heating capabilities.

The proper flow of current to heating section 62, which is selected in the design of heater 38, raises the temperature of the sensor element such that the air/fuel ratio can be adequately controlled immediately after startup of an engine (not shown) into which the sensor element incorporating heater 38 is installed and before the engine reaches its operating temperature. Because thermistors 61, 63 are resistive, the application of a current therethrough causes heat to be generated by each pattern 64, 66. The flow of current is effectuated through heater leads 68, which are disposed on the end portions of edge pattern 64 of first thermistor 61 and are each connectable to a power source (not shown) that provides a flow of current to heating section 62.

Thermistors 61, 63 each typically comprise a precious metal that may be deposited onto substrate 52 in a myriad of ways including, but not limited to, sputtering, chemical vapor deposition, stenciling, and screen printing. Thicker depositions of material are generally screen printed or stenciled onto substrate 52, while thinner depositions of material are generally sputtered or deposited using vapor deposition techniques. In a preferred embodiment, the metal is formed into a paste, screen printed onto substrate 52, and dried. The metal is typically combined with cellulose, a binder, and a solvent to make the paste. Once the paste is applied to the substrate, dried, and sintered onto the substrate, each pattern 64, 66 is about 5 microns to about 50 microns thick. A preferred thickness for each pattern 64, 66 is about 10 to about 40 microns thick.

Variations in the TCRs of each pattern allow the heating characteristics thereof to be substantially self-adjusting. These variations in the TCRs are effectuated by the use of dissimilar materials for thermistors 61, 63. The TCR, which is typically measured in parts per million per degree temperature, is characterized by an increase in resistance for each degree increase of temperature over a given range. Materials having a high TCR are typically used for center pattern 66 so that a greater change in resistance per degree temperature can be realized. Because the heat gradient is preferably from the innermost portions of sensor to the outermost portions, materials having a TCR lower than the TCR of center pattern 66 are typically used for edge pattern 64. In such an instance, as the temperature of center pattern 66 increases, the TCR of the material from which center pattern 66 is fabricated causes a higher resistance to be realized by the material of center pattern 66. When this higher resistance is realized, the current through center pattern 66 is reduced, which in turn reduces the heat generated by center pattern 66. When the heat generated is reduced, the disparity in temperatures between center pattern 66 and edge pattern 64 is minimized and a more uniform temperature profile across the surface of heater 38 is attained. Uniformity in the profile across the surface of heater 38 minimizes tensile stresses that result from the differing rates of expansion associated with heating section 62.

The variations in the TCRs of each pattern 64, 66 can be realized through appropriate selection of conductor materials. The preferred material for center pattern 66 includes, but is not limited to, platinum, which has an inherent TCR of about 3928 ppm/° C. The preferred material for edge pattern 64 includes, but is not limited to, a blend of platinum and palladium. The preferred materials for leads 68 include, but are not limited to, nickel, blends of nickel and chromium, and blends of nickel, chromium, and gold.

In a preferred embodiment, the power source for heater 38 supplies battery voltage to patterns 64, 66, the voltage supplied typically being about 13.5 volts DC. Because the voltage is substantially constant over each leg of pattern 64, 66, and because the resistance of each pattern 64, 66, is variable and dependent upon the temperature thereof, the current flowing through each pattern 64, 66 is likewise variable and is defined by the equation I=E/R.

Figure 3:
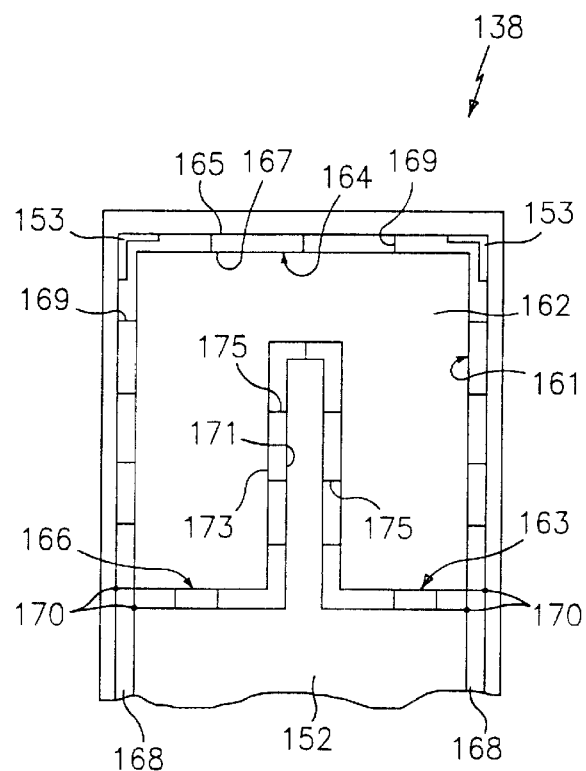
FIG. 3 is a plan view of a second embodiment of a heater pattern disposed on a substrate.

Referring now to FIG. 3, an alternate embodiment of a heater is shown generally at 138 in which an alternate embodiment of a heater pattern is shown. In heater 138, a first thermistor 161 and a second thermistor 163 are arranged so as to define parallel conductor paths that are utilized to eliminate the presence of "hotspots" within a heating section 162 disposed on a substrate 152. Hotspots are typically caused by variations in the cross sectional area of the conductor over a given length and result during the process of depositing the pattern on the substrate. In such an instance, current is forced through conductors having cross sectional areas of varying size, which results in localized areas of increased resistance in the conducting medium. Because of the TCR of the conductor material, the resultant localized increases in resistance subsequently cause localized increases in temperature. The heat generated by the temperature increases is directly proportional to the resistance of the conductor; therefore, the localized increases in temperature result in the appearance of hotspots. However, because the driving force for heat transfer is a temperature differential, as the temperature of the hotspot increases, the rate at which heat is transferred from the hotspot also increases. Nevertheless, the hotspot remains at a substantially higher temperature than its surroundings. Because many of the mechanisms responsible for early failures of sensor elements are exponentially accelerated by high temperature conditions, it is desirable to minimize the probability that hotspots will occur in any heater pattern.

Heating section 162 comprises an edge pattern, shown generally at 164, and a center pattern, shown generally at 166. Edge pattern 164 extends generally about an outer edge of heating section 162 that corresponds with a perimeter of substrate 152 and comprises a first conductor 165 and a second conductor 167 disposed in a spaced relationship. In a preferred embodiment, conductors 165, 167 are in electronic communication with each other at various intervals along the lengths thereof through a plurality of cross conductors 169, which are disposed between conductors 165, 167 so as to cause edge pattern 164 to resemble a ladder.

Because the length of the path of first conductor 165 is necessarily longer than the length of the path of second conductor 167, first conductor 165 (assuming that conductors 165, 167 are substantially equal in cross sectional area) has a higher resistance than second conductor 167. First conductor 165 is, therefore, configured such that the portions thereof at corners 153 include additional conductor material, thereby rendering first conductor 165 thicker at corners 153. By dimensioning the portions of first conductor 165 to have thicker cross sectional areas (i.e., the portions proximate corners 153), the resistances of both conductors 165, 167 can be equalized.

Center pattern 166 extends in an electrically parallel configuration relative to edge pattern 164 substantially across a portion of heating section 162 intermediate the perimeter of substrate 152. Center pattern 166 comprises a first conductor 171 and a second conductor 173, which are in communication with each other at various intervals along the lengths thereof through a plurality of cross conductors 175. In a preferred embodiment, center pattern 166 is arranged on substrate 152 in the form of an inverted U shape, the ends of the legs of the U shape being in electronic communication with nodes 170. Such an arrangement optimizes the area of substrate 152 over which center pattern 166 is disposed, thereby minimizing the area not in direct contact with center pattern 166. Minimization of the area of substrate 152 not in direct contact with either edge pattern 164 or center pattern 166 reduces the number of temperature differentials (and, therefore, the number of hotspots) created within heating section 162 and provides heater 138 with improved heating capabilities.

As in the first embodiment, the heat gradient is preferably from the innermost portions of sensor to the outermost portions; therefore, materials having lower TCRs are typically used for edge pattern 164, while materials having higher TCRs are typically used for center pattern 166. In such an instance, as the temperature of second thermistor 163 increases, the TCR of the material from which second thermistor 163 is fabricated causes a higher resistance to be realized by center pattern 166. When this higher resistance is realized, the current through second thermistor 163 is reduced, which in turn reduces the heat generated by second thermistor 163. Furthermore, because of the "ladder" pattern defined by conductors 165, 167, 169 and conductors 171, 173, 175, the number and frequency of appearance of hotspots are minimized, which also contributes to the reduction of heat generation. When the heat generated is reduced, the disparity in temperatures between center pattern 166 and edge pattern 164 is minimized and a more uniform temperature profile across the surface of heater 138 is attained. Uniformity in the profile across the surface of heater 138 minimizes tensile stresses that result from the differing rates of expansion associated with heating section 162. As in the main embodiment shown in FIG. 2, each pattern 164, 166 is typically deposited onto substrate 152 at a thickness of about 5 microns to about 50 microns, with about 10 microns to about 40 microns being preferred.

As above, thermistors 161, 163 may be deposited onto substrate 152 in a myriad of ways including, but not limited to, sputtering, chemical vapor deposition, stenciling, and screen printing. Thicker depositions of material are generally screen printed or stenciled onto substrate 152, while thinner depositions of material are generally sputtered or deposited using vapor deposition techniques. Also, as above, second thermistor 163 is preferably fabricated from materials having a high TCR value such as platinum. Materials of construction for first thermistor 161 are typically materials having a TCR value lower than that of center pattern 166, such as platinum/palladium blends. Leads 168, which are disposed on the ends of edge pattern 164, are typically nickel/chromium blends or nickel/chromium/gold blends.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

What is claimed is:

1. A heater for a gas sensor, comprising:
a thermistor element comprising a first conductor, a second conductor extending substantially parallel to said first conductor, and a plurality of cross conductors extending between said fit conductor and said second conductor; wherein said thermistor extends about a perimeter of a substrate with said first conductor disposed external to said second conductor, and wherein said first conductor comprises a first portion having a thicker cross sectional area than a second portion.

2. A method for operating a heater for a gas sensor, comprising:
passing electrical current through a first thermistor element, wherein said first thermistor element comprises a first conductor, and a second conductor extending substantially parallel to said first conductor; and
reducing a number of hot spots with a cross conductor extending between said first conductor and said second conductor.

3. A gas sensor element, comprising:
an electrochemical cell; and
a heater disposed on a substrate and in thermal communication with said electrochemical cell, said heater comprising a first thermistor element extending about a perimeter of said substrate, and a second thermistor element extending across a portion of said substrate intermediate said perimeter of said substrate, wherein said first thermistor element and said second thermistor element are arranged in an electrically parallel configuration, and wherein said second thermistor element has a higher thermal coefficient of resistance than said first thermistor element.

4. The gas sensor element of claim 3, wherein said first thermistor element comprises,
a first conductor,
a second conductor extending substantially parallel to said first conductor, and
a plurality of cross conductors extending between said first conductor of said first thermistor element and said second conductor of said first thermistor element.

5. The gas sensor element of claim 4, wherein said second thermistor element comprises,
a first conductor,
a second conductor extending substantially parallel to said first conductor, and
a plurality of cross conductors extending between said first conductor of said second thermistor element and said second conductor of said second thermistor element.

6. A method for operating a heater in a gas sensor element, comprising:
introducing a first electrical current to a first thermistor element, wherein said first thermistor element extends about a perimeter of said substrate;
introducing a second electrical current to a second thermistor element extending across a portion of said substrate intermediate said perimeter of said substrate, wherein said first thermistor element and said second thermistor element are arranged in an electrically parallel configuration, and wherein said second thermistor element has a higher thermal coefficient of resistance than said first thermistor element; and
reducing said second electrical current to said second thermistor element.

7. The method of claim 3, further comprising reducing a number of hot spots with a cross conductor extending between said first conductor and said second conductor.

* * * * *